(12) United States Patent  
Sharrow et al.

(10) Patent No.: US 7,651,578 B2
(45) Date of Patent: Jan. 26, 2010

(54) GUIDEWIRE WITH POLYMER JACKET AND METHOD OF MAKING

(75) Inventors: James S. Sharrow, Bloomington, MN (US); Brian R. Reynolds, Ramsey, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 362 days.

(21) Appl. No.: 11/449,166

(22) Filed: Jun. 8, 2006

(65) Prior Publication Data

US 2007/0299366 A1 Dec. 27, 2007

(51) Int. Cl.
- B29C 49/00 (2006.01)
- B60J 10/00 (2006.01)
- B29C 65/00 (2006.01)
- B32B 37/00 (2006.01)
- B65C 9/25 (2006.01)
- C09J 5/00 (2006.01)
- A61B 5/00 (2006.01)
- A61M 25/00 (2006.01)
- A61M 5/178 (2006.01)
- A61F 11/00 (2006.01)

(52) U.S. Cl. .......... 156/198; 156/221; 156/294; 156/323; 600/585; 604/164.13; 606/108

(58) Field of Classification Search .......... 156/84, 156/85, 86, 196, 198, 199, 221, 293, 294, 156/247, 248, 269, 270, 271, 323; 600/585; 604/164.01, 164.08, 434, 164.13; 606/108

See application file for complete search history.

(56) References Cited

U.S. PATENT DOCUMENTS

| 4,462,946 | A | * | 7/1984 | Goldsworthy | ............ 264/442 |
| 4,895,168 | A | | 1/1990 | Machek | |
| 5,040,543 | A | | 8/1991 | Badera et al. | |
| 5,267,574 | A | | 12/1993 | Viera et al. | |
| 5,333,620 | A | * | 8/1994 | Moutafis et al. | ............ 600/585 |
| 5,335,410 | A | * | 8/1994 | Burnham | ................. 29/452 |
| 5,368,049 | A | | 11/1994 | Raman et al. | |
| 5,409,015 | A | | 4/1995 | Palermo | |
| 5,443,455 | A | | 8/1995 | Hergenrother et al. | |
| 5,443,907 | A | | 8/1995 | Slaikeu et al. | |
| 5,452,726 | A | | 9/1995 | Burmeister et al. | |
| 5,772,609 | A | | 6/1998 | Nguyen et al. | |
| 5,836,893 | A | | 11/1998 | Urick | |
| 5,924,998 | A | | 7/1999 | Cornelius et al. | |
| 5,984,878 | A | | 11/1999 | Engelson | |

(Continued)

FOREIGN PATENT DOCUMENTS

JP 02064374 A * 3/1990

(Continued)

*Primary Examiner*—Jeff H Aftergut
*Assistant Examiner*—Brian R Slawski
(74) *Attorney, Agent, or Firm*—Crompton, Seager & Tufte, LLC

(57) ABSTRACT

A guidewire and methods for making and using the same. The guidewire may include a core wire and a polymer jacket attached to the core wire. The guidewire may be manufactured by advancing the core wire, polymer jacket, and a tooling tube through a heated die assembly so as to heat and compress the polymer jacket onto the core wire. Optionally, the tooling tube may be removed from the jacket after advancing the components through the die assembly.

21 Claims, 6 Drawing Sheets

U.S. PATENT DOCUMENTS

| | | | |
|---|---|---|---|
| 6,106,485 A * | 8/2000 | McMahon | 600/585 |
| 6,139,510 A | 10/2000 | Palermo | |
| 6,193,686 B1 | 2/2001 | Estrada et al. | |
| 6,251,085 B1 | 6/2001 | Tezuka | |
| 6,251,086 B1 | 6/2001 | Cornelius et al. | |
| 6,296,616 B1 | 10/2001 | McMahon | |
| 6,340,441 B1 | 1/2002 | Meyer et al. | |
| 6,402,706 B2 | 6/2002 | Richardson et al. | |
| 6,409,682 B1 | 6/2002 | Burmeister et al. | |
| 6,419,745 B1 * | 7/2002 | Burkett et al. | 118/125 |
| 6,432,066 B1 | 8/2002 | Ferrera | |
| 6,461,311 B2 | 10/2002 | DuBois et al. | |
| 6,488,637 B1 | 12/2002 | Eder et al. | |
| 6,494,847 B1 | 12/2002 | Richardson et al. | |
| 6,579,246 B2 | 6/2003 | Jacobsen et al. | |
| 6,595,932 B2 | 7/2003 | Ferrera | |
| 6,612,998 B2 | 9/2003 | Gosiengfiao et al. | |
| 6,656,134 B2 | 12/2003 | Cornelius et al. | |
| 6,669,652 B2 | 12/2003 | Anderson et al. | |
| 6,673,025 B1 | 1/2004 | Richardson et al. | |
| 6,918,882 B2 | 7/2005 | Skujins et al. | |
| 2003/0032897 A1 | 2/2003 | Burmeister et al. | |
| 2003/0060757 A1 | 3/2003 | Wantink et al. | |
| 2003/0069521 A1 | 4/2003 | Reynolds et al. | |
| 2004/0039307 A1 | 2/2004 | Ferrera | |
| 2004/0054301 A1 | 3/2004 | Cassell et al. | |
| 2004/0059258 A1 | 3/2004 | Campion et al. | |
| 2004/0142643 A1 | 7/2004 | Miller et al. | |
| 2004/0167437 A1 | 8/2004 | Sharrow et al. | |
| 2004/0167439 A1 | 8/2004 | Sharrow | |
| 2004/0167441 A1 | 8/2004 | Reynolds et al. | |
| 2004/0167442 A1 | 8/2004 | Shireman et al. | |
| 2005/0038358 A1 | 2/2005 | Furukawa | |
| 2005/0096665 A1 * | 5/2005 | Reynolds et al. | 606/108 |
| 2006/0198976 A1 * | 9/2006 | Trapp | 428/36.9 |

FOREIGN PATENT DOCUMENTS

| | | |
|---|---|---|
| WO | 9300953 | 1/1993 |
| WO | WO 9527576 A1 * | 10/1995 |

* cited by examiner

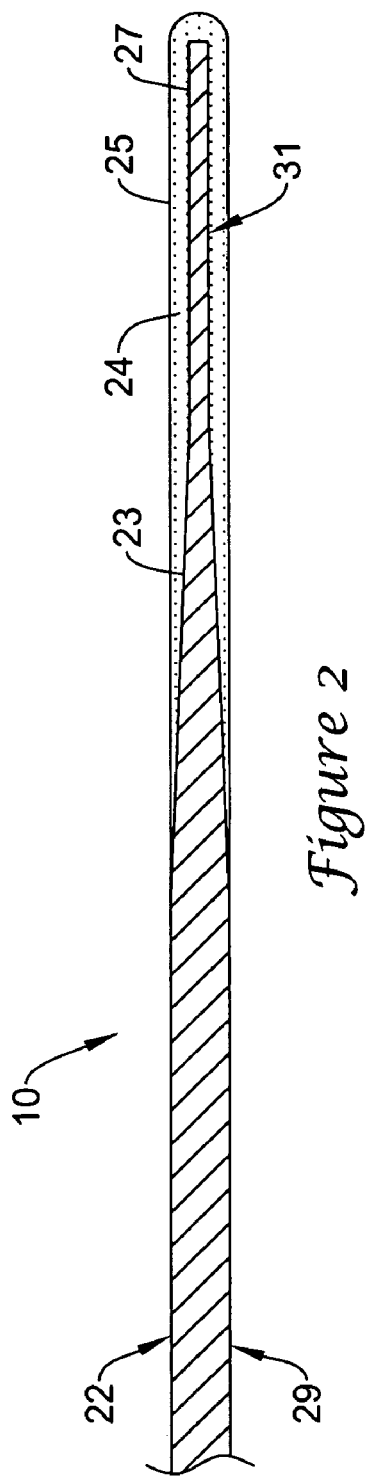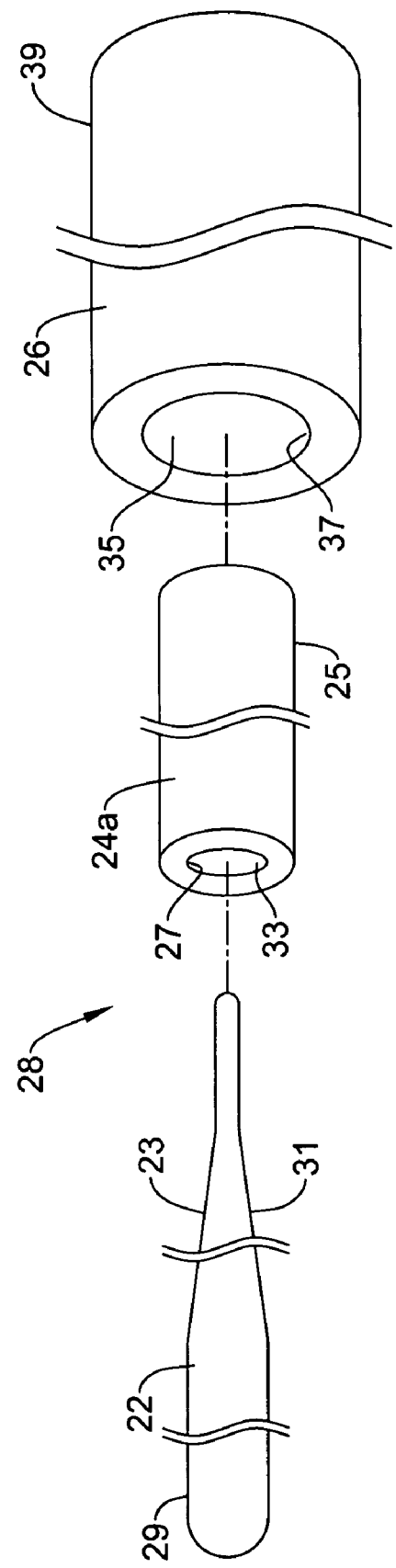

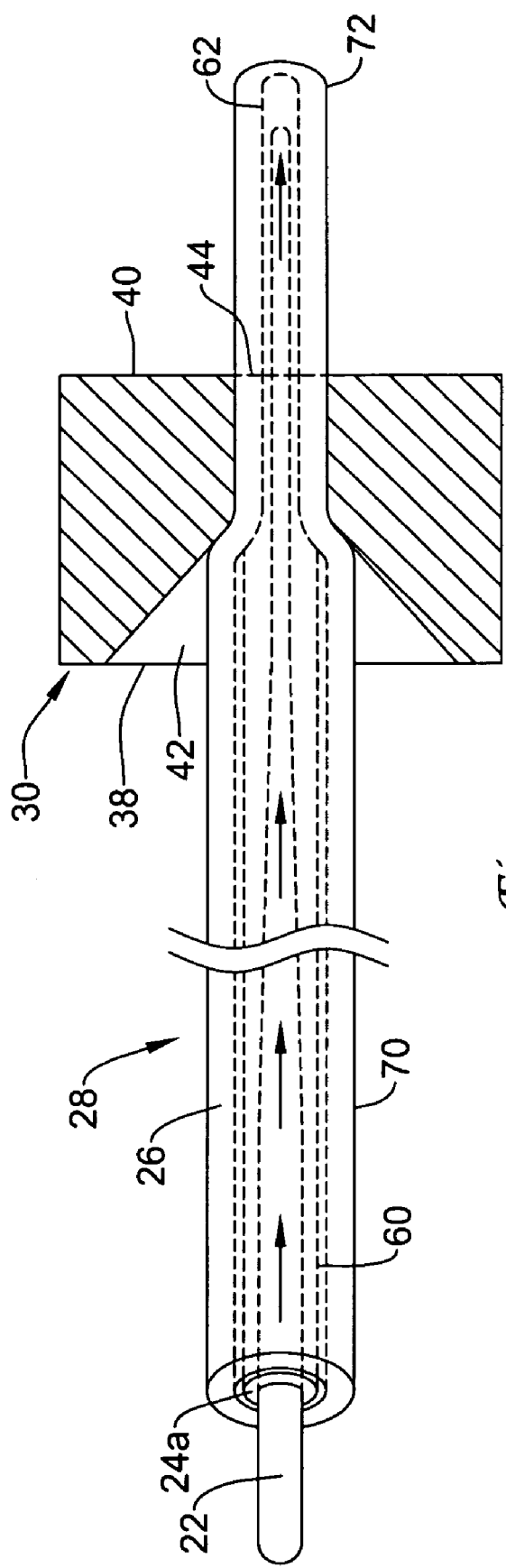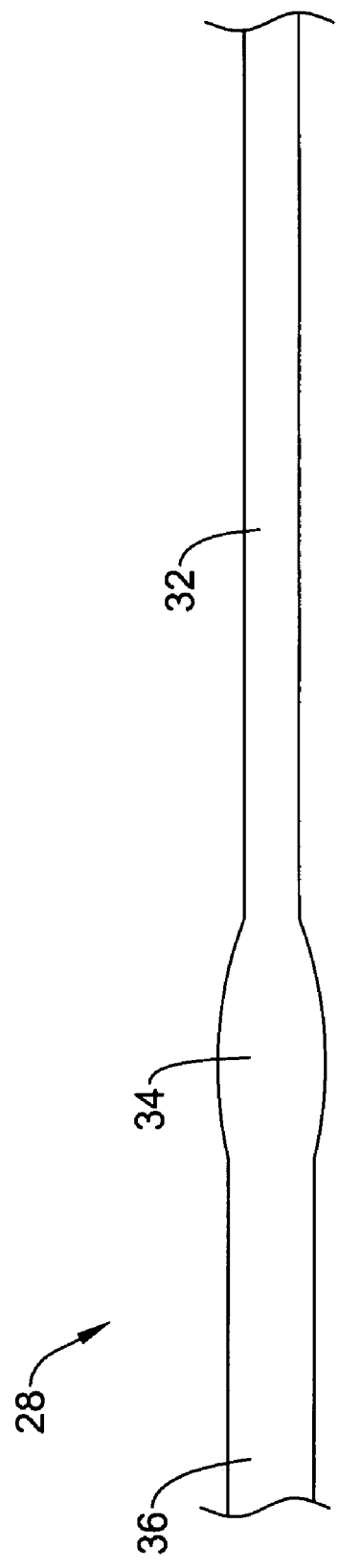
Figure 4
Figure 5

GUIDEWIRE WITH POLYMER JACKET AND METHOD OF MAKING

FIELD OF THE INVENTION

The invention relates to medical devices, for example, intracorporal medical devices, and methods for manufacturing such medical devices. More particularly, the invention relates to guidewires and methods for manufacturing guidewires that include a polymer jacket disposed about a core member.

BACKGROUND

A wide variety of intracorporal medical guidewires have been developed for medical use, for example, intravascular use. These guidewires may include a variety of structures and are manufactured by any one of a variety of different manufacturing methods. Of the known guidewires and manufacturing methods, each has certain advantages and disadvantages. There is an ongoing need to provide alternative guidewire constructions and manufacturing methods.

BRIEF SUMMARY

The invention provides design, structural, material, and manufacturing method alternatives for medical devices, for example, guidewires. Some example guidewires can include a core member, such as a core wire, having a polymer jacket disposed about and attached to a portion thereof. In some embodiments, the polymer jacket is attached to the core wire using a method which includes disposing a polymer member adapted to become the polymer jacket about a portion of the core wire, disposing an outer tubular member about at least a portion of the polymer member, and applying a predetermined amount of heat and compressive force to the outer tubular member to attach the polymer member to the core wire and form the polymer jacket. In some embodiments, the outer tubular member can be thereafter removed, leaving a core wire having polymer jacket disposed about and attached to a portion thereof. In some embodiments, the outer tubular member can remain disposed on at least a portion of the polymer jacket, leaving a core wire having polymer jacket disposed about and attached to a portion thereof, and an outer tubular member disposed about and attached to a portion of the polymer jacket.

The above summary of some embodiments is not intended to describe each disclosed embodiment or every implementation of the present invention. The Figures, and Detailed Description, which follow, more particularly exemplify these embodiments.

BRIEF DESCRIPTION OF THE DRAWINGS

The invention may be more completely understood in consideration of the following detailed description of various embodiments of the invention in connection with the accompanying drawings, in which:

FIG. 2 is a cross-sectional side view of an example embodiment of a guidewire;

FIG. 3 is an exploded view of an example core wire, a polymer jacket member, and an elongated tubular member that may be used in a method of manufacturing a guidewire, for example, the guidewire of FIG. 2;

FIG. 4 is a side view depicting an example manufacturing method for manufacturing a guidewire;

FIG. 5 is a side view of an example subassembly after partially passing through a shaping die;

Figure 1:
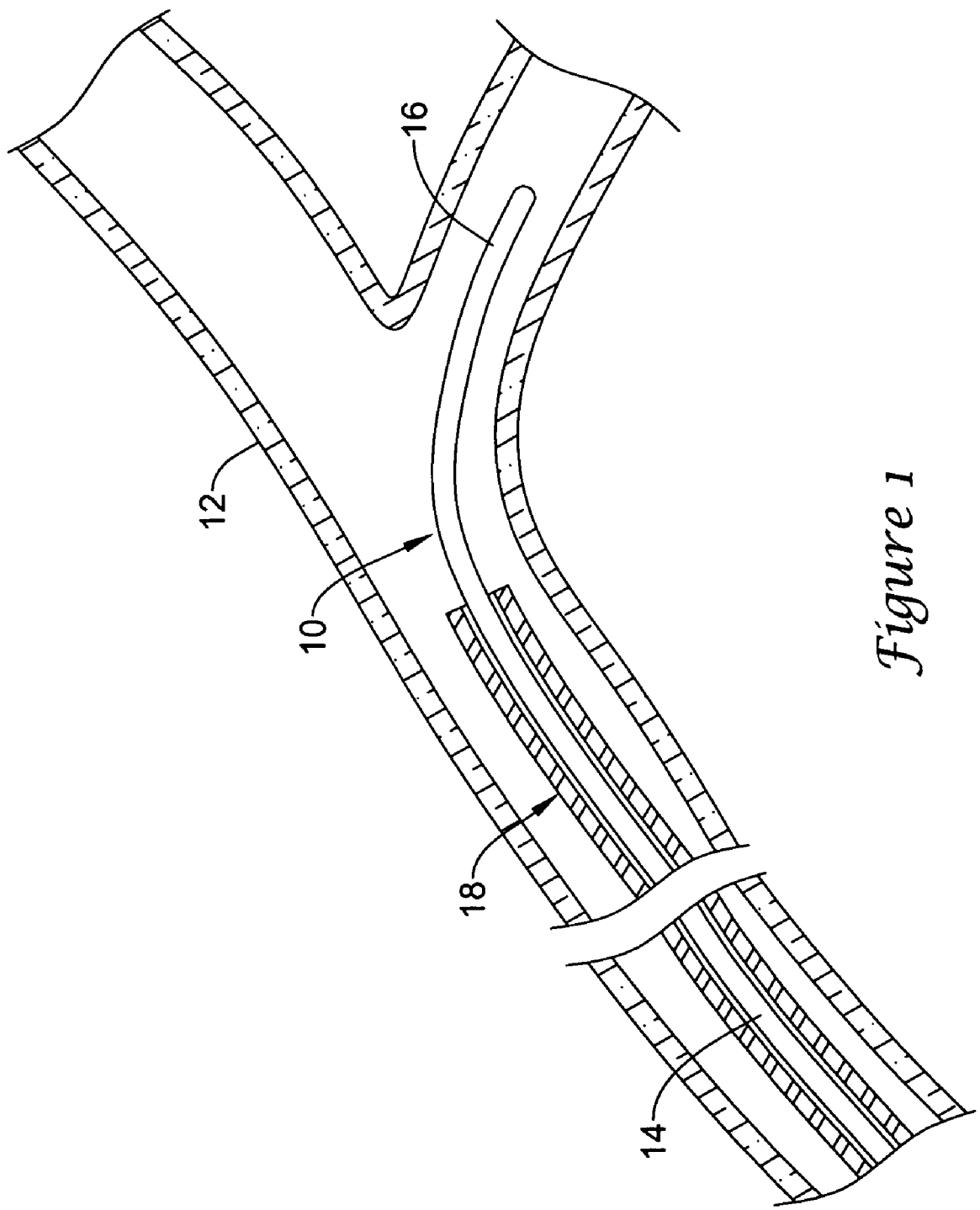
FIG. 1 is a partial cross-sectional plan view of an example guidewire disposed in a blood vessel.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION

The following description should be read with reference to the drawings wherein like reference numerals indicate like elements throughout the several views. The detailed description and drawings illustrate example embodiments of the claimed invention.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

The following detailed description should be read with reference to the drawings in which similar elements in different drawings are numbered the same. The drawings, which are not necessarily to scale, depict illustrative embodiments and are not intended to limit the scope of the invention.

Refer now to FIG. 1, which is a plan view of a generic example of a guidewire 10 disposed in the anatomy of a patient, for example, in a blood vessel 12. Guidewire 10 may include a proximal section 14 and a distal section 16, and can be generally configured for advancement within the anatomy of a patient. For example, the guidewire 10 may be used for intravascular procedures according to common practice and procedure. For example, guidewire 10 may be used in conjunction with another medical device such as a catheter 18, or any of many other medical devices. Of course, numerous other uses are known amongst clinicians for guidewires and other similarly configured medical devices.

Refer to FIG. 2, which shows an example embodiment of a guidewire 10 including an elongated core member, such as a core wire 22, extending along a longitudinal axis and including an outer surface 23. The core wire 22 includes a proximal portion 29 and a distal portion 31. A polymer member, such as a thermoplastic polymer jacket 24, is connected about a portion of the core wire 22. The polymer jacket 24 includes an outer surface 25 and an inner surface 27. The inner surface 27 mates with and is attached to the outer surface 23 of the core wire 22. In the embodiment shown, the distal portion 31 of the core wire 22 is tapered, and the polymer jacket 24 is connected about the tapered distal portion 31 of the core wire 22, and does not extend over the proximal portion 29. Additionally, the polymer jacket 24 includes an outer diameter that is generally about the same as the outer diameter of the proximal portion 29 of the core wire 22—thereby providing for a generally smooth transition between the polymer jacket 24 and the proximal portion 29. It will be understood by those of skill in the art and others, however, that the polymer jacket 24 may be connected about the core wire 22 in any of a broad variety of other positions and/or configurations, and that the particular embodiment shown in FIG. 2 is by way of example only. For example, the polymer jacket 24 may extend over the entire length of the core wire 22, may extend only about a portion of the distal and/or proximal portions 29/31, may or may not be disposed such that it begins or ends relative to any tapers or constant diameter portions of the core wire 22, or may include any thickness or outer diameter that is deemed to be desired or useful. Additionally, the outer diameter of the polymer jacket 24 may be constant or tapered, and may or may not mate up or be sized relative to portions of the core wire 22 to provide for smooth transitions.

In at least some embodiments, some aspects of the invention relate to a method or process of making a guidewire, and can involve a method or process used to connect or affix the polymer jacket 24 on a portion of the core member 22. Some such methods generally involve disposing a portion of a polymer jacket member about a portion of the core wire, and disposing an additional member, such as an elongated tubular member, about a portion of the polymer jacket member to form a subassembly. Heat and a compressive force are then applied to the subassembly, for example, to the outer surface of the elongated tubular member. The heat softens the polymer jacket member and the compressive force acts to deform and attach the polymer jacket member to the core member such that it forms a polymer jacket disposed on the core member. For example, in some embodiments, the subassembly can be passed through a heated die that applies the necessary heat and compressive force to the subassembly. The elongated tubular member can be adapted and/or configured to act as a forming member and/or retaining member and/or tooling member and/or outer barrier during the method to aide in attaching the polymer jacket member to the core member and aid in providing the polymer jacket with desired characteristics, such as shape and size. In some embodiments, the elongated tubular member can be removed after the polymer jacket is attached to the core wire, while in other embodiments, the elongated tubular member can remain on the guidewire. Some example embodiments of such a method are discussed in more detail below.

For example, refer now to FIGS. 3, 4, and 5, which can be used in describing an example embodiment of such a method and/or process wherein a polymer jacket 24 is attached and/or affixed about the core wire 22. As can be seen in FIG. 3, a core wire 22, a polymer jacket member 24a, and an additional member, such as an elongated tubular member 26 can be provided, for example, as three separate members. These three components can be used to create a subassembly 28 that can be used in performing an example embodiment of a method of attaching the polymer jacket 24 to the core wire 22, as will be discussed in more detail below. FIG. 3 is an exploded view of the subassembly 28. However, prior to describing some examples of performing the method, a description of at least some of the components of the subassembly 28 will be provided.

The core wire 22 can include structure and materials as are generally known for use as a core wire in a guidewire. For example, the core wire 22 may include one unitary member, or may include multiple pieces or portions connected together to form the core wire, wherein such pieces and/or portions may be made of the same or different materials. Core wire 22 can have a solid cross-section, a hollow cross-section or combinations of areas having solid cross-sections and hollow cross sections. The core wire 22 can have any of a broad variety of cross-sectional shapes, for example, round, flattened, oval, rectangular, square, polygonal, and the like, or any other suitable shape. The cross-sectional shape can be constant or can vary. The core wire 22 may have a generally constant outer diameter, or may include one or more tapers and/or tapered regions, which may be linearly tapered, tapered in a curvilinear fashion, uniformly tapered, non-uniformly tapered, or tapered in a step-wise fashion. The core wire 22 may be made from any suitable material including, for example, metals, metal alloys, polymers, composites, or the like. Some examples of suitable metals and metal alloys include stainless steel, such as 304V, 304L, and 316L stainless steel; alloys including nickel-titanium alloy such as linear elastic or superelastic (i.e. pseudoelastic) nitinol; nickel-chromium alloy; nickel-chromium-iron alloy; cobalt alloy; tungsten or tungsten alloys; MP35-N (having a composition of about 35% Ni, 35% Co, 20% Cr, 9.75% Mo, a maximum 1% Fe, a maximum 1% Ti, a maximum 0.25% C, a maximum 0.15% Mn, and a maximum 0.15% Si); hastelloy; monel 400; inconel 625; or the like; or other suitable material, or combinations or alloys thereof. In addition, the core wire 22 may include joints made of the same or other materials (including, for example, solder), welds, etc. The material of the core wire may include generally linear elastic properties, or may include properties such as super-elasticity (pseudoelasticity) and/or shape memory. Some example embodiments of guidewire constructions, including core wire materials, size, shape, tapers, methods of manufacture and/or construction, tip constructions, and the like, are shown and described in U.S. Pat. Nos. 6,579,246 and 6,918,882; and U.S. patent application Ser. No. 10/086,992 filed Feb. 28, 2002 (Pub. No. U.S. 2003/0069521; Ser. No. 10/346,698 filed Jan. 17, 2003 (Pub. No. U.S. 2004/0142643); Ser. No. 10/375,493 filed Feb. 26, 2003 (Pub. No. U.S. 2004/0167437); Ser. No. 10/375,766 filed Feb. 26, 2003 (Pub. No. U.S. 2004/0167441); and Ser. No. 10/376,068 filed Feb. 26, 2003 (Pub. No. U.S. 2004/0167442), the entire disclosures of which are expressly incorporated herein by reference.

In at least some embodiments, core wire 22 may take the form of or include a nickel-titanium alloy tube. The tube may include a plurality of slots that, for example, allow the tube to be both flexible and torque-transmitting. Polymer jacket 24 can be disposed on the tube in a manner similar to what is described herein. For example, in embodiments where core wire 22 includes a nickel-titanium alloy tube attached thereto, polymer jacket 24 can be disposed over all or portions of core wire 22, the tube, or both. In addition, some embodiments include polymer jacket 24 covering only the proximal section of the tube (and either terminating at the proximal end or extending therefrom), covering only the distal section of the tube (and either terminating at the distal end or extending therefrom), covering the whole length of the tube, covering the whole length of the tube and extending beyond the distal or proximal end of the tube, disposed distally of the tube, disposed proximally of the tube, or disposed at any other suitable location.

The polymer jacket member 24*a* can be an elongated structure defining a channel or lumen 33 that is sized or otherwise adapted to receive at least a portion of the core wire 22. As such, at least a portion of the polymer jacket member 24*a* may adapted and/or configured to be disposed about at least a portion of the core wire 22. As will be seen below, the polymer jacket member 24*a* will become the polymer jacket 24 disposed and/or attached to the core wire 22. In some embodiments, a number of additional structures may be embedded within polymer jacket 24 such as a coil, braid, and the like.

In the embodiment shown, the polymer jacket member 24*a* is a generally elongated tubular member defining a lumen 33. The lumen 33 may or may not be centered along the longitudinal axis of the jacket member 24*a*. As shown, the polymer jacket member 24*a* has a generally circular cross-sectional shape, but as will be understood by those of skill in the art and others, other shapes may be used, sometimes depending upon the desired shape of the final polymer jacket 24. For example, other cross-sectional shapes such as oval, oblong, triangular, rectangular, polygonal, or the like may be used.

In some embodiments, the polymer jacket member 24*a* can be a generally tubular member having an outer diameter in the range of about 0.0015 to about 0.05 inches, or about 0.01 to about 0.02 inches, or about 0.015±0.0015 inches or so and a lumen 33 having a diameter in the range of about 0.0015 to about 0.05 inches, or about 0.02 to about 0.03 inches, or about 0.025±0.0001 inches or so. It should be understood, however, that these sizes and shapes are given by way of example only, and that a broad variety of other sizes and shapes may be used.

The polymer jacket member 24*a* can include materials generally known for use as a polymer jacket on a guidewire, and that can be disposed about the core wire 22 using the methods described herein. For example, the polymer jacket member 24*a* can include and/or be made of a polymer material, such as a thermoplastic polymer material, that can be heated to a predetermined temperature at or above which the material can be molded into the desired shape, attached to the outer surface 23 of the core wire 22, and cooled so that it sets in the desired shape. For example, the polymer jacket member 24*a* may include material that has a predetermined "softening point temperature" at or above which the material becomes at least partially "visco-elastic" and/or can be easily deformed and attached to the core wire 22. By visco-elastic, it can be meant that the material responds to a deforming load by combining both viscous and elastic qualities. In at least some embodiments, the material of the polymer jacket member 24*a*, when at the "softening point temperature" has sufficient rheological properties, such as plasticity, that the material can be permanently deformed under a predetermined compressive force and can be attached to the core wire 22.

As is generally known, the melting point of a polymer does not occur over a sharp temperature range (for example a 1 to 2° C. range) as is generally observed for small organic molecules. There is usually a greater temperature range over which the viscosity of the polymer slowly changes from that of a solid to that of a liquid. Technically, only crystalline polymers have a true melting point; that's the temperature at which the crystallites melt and the total mass of plastic becomes amorphous. Amorphous polymers do not have a true melting point; however, they do have a first-order transition where their mechanical behavior transitions from a rubbery nature to viscous rubbery flow. As such, the terms "softening point" or "softening point temperature" can be used. The softening point temperature can indicate the temperature at which the polymer becomes sufficiently visco-elastic and/or deformable and/or flowable such that under the predetermined compressive force applied during the method, the polymer jacket member 24*a* can be attached to the core wire 22.

It should be understood that at some increased temperature the polymer material will become so soft that it will flow under very low pressure. This is the final transition to a viscous rubbery flow. This can be considered the "melting" or "liquid" temperature of the polymer, or the first-order transition temperature. Generally the softening point temperature for a given polymer occurs at a temperature below that of the melting or liquid temperature of the polymer. However, it is conceivable that in some embodiments, the softening point temperature and the melting or liquid temperature of a particular polymer may be very close, or possibly the same.

As is also generally known, amorphous polymers (or crystalline polymers having some amorphous portion) have a glass transition region(s) and a glass transition temperature(s) ($T_g$) at which point the material changes from a brittle vitreous state to a rubbery state. This change in behavior is sometimes evidenced by a sharp decline in modulus (stiffness), or increase in impact strength as the ambient temperature is increased. The region of transition is termed the glass transition region, and the temperature at the midpoint of the transition from glassy to rubbery, the glass transition region, is defined as the glass transition temperature, $T_g$.

While the softening point temperature and the $T_g$ of a polymer material may be at least somewhat related, in at least some embodiments, the softening point temperature of the material used in the polymer jacket member 24*a* is above that of the $T_g$. As can be appreciated, the softening point temperature relates to the material becoming sufficiently plastic or visco-elastic such that the material can be easily deformed and attached to the core wire 22, wherein the $T_g$ point indicates the changes from a brittle vitreous state to a rubbery state. However, it is conceivable that in some embodiments, the softening point temperature and the $T_g$ of a particular polymer may be close, or possibly the same.

In some embodiments, the polymer jacket member 24*a* can include and/or be made of a polymer material, such as a thermoplastic polymer material, that has a softening point in the range of about −55 to about 290° C. or in the range of about −24 to about 62° C. Additionally, in at least some embodiments, the polymer jacket member 24*a* can include and/or be made of a material, such as a thermoplastic material, that has a $T_g$ in the range of about −55 to about 400° C., in the range of about −55 to about 290° C., or in the range of about −24 to about 62° C. Additionally, in at lest some embodiments, the polymer jacket member 24*a* can include and/or be made of a material, such as a thermoplastic material, that has a "melting" or "liquid" temperature in the range of about −55 to about 600° C. These ranges can vary, for example, depending on the type or level of loading.

Some examples of suitable thermoplastic polymers may include polyurethanes, nylons, phenylene oxides, polyesters, polyether-esters, polyethylenes, polypropylenes, polyamides, polyimides, polyetherimides, silicones, fluoropolymers (for example FEP, PFA, etc.), or combinations, copolymers, or blends thereof, or the like. Some example may include polyoxymethylene (POM), polybutylene terephthalate (PBT), polyether block ester, polyvinylchloride (PVC), polyether-esters such as a polyether-ester elastomer such as ARNITEL® available from DSM Engineering Plastics, polyesters such as a polyester elastomer such as HYTREL® available from DuPont; polyamides such as DURETHAN® available from Bayer or CRISTAMID® available from Elf Atochem, elastomeric polyamides, block polyamide/ethers, polyether block amide (PEBA, for example, available under the trade name PEBAX®), polyethylenes such as Marlex high-density polyethylene, Marlex low-density polyethylene, linear low density polyethylene (for example, REXELL®), polyethylene terephthalate (PET), polyetheretherketone (PEEK), polyphenylene sulfide (PPS), polyphenylene oxide (PPO), polysulfone, or combinations, copolymers, or blends thereof, or the like.

In some embodiments, other materials may also be combined with the polymer material to achieve desired properties. For example, in some embodiments, the polymer material may be loaded with or include a radiopaque material to aid in visualizing the guidewire during use, for example, under fluoroscopy. For example, the polymer material may be loaded with tungsten, bismuth subcarbonate, barium sulfate, or other suitable materials, or mixtures or combinations thereof, or the like. Similarly, some embodiments may include materials that may increase the strength, flexibility, rigidity, or other characteristics of the polymer. For example, the polymer may be blended or mixed with a liquid crystal polymer (LCP). For example, the mixture can contain up to about 5% LCP.

Referring back to FIG. 3, the elongated tubular member 26 includes a channel or lumen 35 that is sized or otherwise adapted to receive at least a portion of the polymer jacket member 24a therein. The elongated tubular member 26 includes an inner surface 37 defining the lumen 35, and an outer surface 39.

As indicated above, the elongated tubular member 26, when disposed about the polymer jacket member 24a, can be adapted and/or configured to act as an outer barrier and/or forming member and/or retaining member and/or tooling member for the polymer jacket member 24a when heat and compressive force is applied during the attachment of the polymer jacket member 24a to the core wire 22.

For example, the elongated tubular member 26 can be adapted and/or configured such that when the components are disposed to create the subassembly 28, and a predetermined amount of heat is applied to the outer surface 39, the elongated tubular member 26 can transfer at least some of this heat to the polymer jacket member 24a—thereby allowing the heat to soften the material of the polymer jacket member 24a. Additionally, the elongated tubular member 26 can be adapted and/or configured such that when a predetermined compressive force is applied to the outer surface 39, the elongated tubular member 26 can transfer at least some of this compressive force to the polymer jacket member 24a. For example, the elongated tubular member 26 may include and/or be made of a material that is sufficiently flexible and/or deformable and/or has other rheological characteristics, such as sufficient plasticity, such that when the predetermined compressive force is applied, the elongated tubular member 26 flexes and/or deforms to apply at least some of the compressive force to the polymer jacket member 24a.

The inner surface 37 of the elongated tubular member 26 can be adapted and/or configured such that when the heat and compressive force is applied, the inner surface 37 can aid in shaping and/or forming the polymer jacket member 24a, for example the outer surface 25 of the polymer jacket member 24a, to create the desire polymer jacket 24. For example, the shape and/or texture of the inner surface 37 of the elongated tubular member 26, through the application of the method, can create a general mirror image of itself on the outer surface 25 of the polymer jacket 24. Furthermore, the elongated tubular member 26 can be adapted and/or configured such that when a device, such as a die, is used to apply the compressive force, the elongated tubular member 26 can act as a barrier between the device and the softened polymer jacket member 24a, thereby reducing the likelihood that the device would become fouled with softened polymer and/or reducing the likelihood that the device would mar or otherwise undesirably deform the surface of the softened polymer jacket member 24a. In essence, in at least some embodiments, the elongated tubular member 26 can be adapted and/or configured to act as a mold or form of sorts, such that when heat and compressive force is applied to the subassembly 28, the elongated tubular member 26 can aid in retaining and/or attaching the polymer jacket member 24a to the core wire, and can aid in shaping and/or forming lo the polymer jacket member 24a.

In the embodiment shown, elongated tubular member 26 has a generally circular cross-sectional shape, wherein both the lumen 35 (defined by inner surface 37) and the outer surface 39 have generally circular cross-sectional shape. However, it should be understood that other shapes may be used, for example sometimes depending upon the desired shape of the final polymer jacket 24 and/or the particular mechanism, such as a die or the like, that is used to apply the heat and/or compressive force. For example, other cross-sectional shapes such as oval, oblong, triangular, rectangular, polygonal, or shapes having bumps, grooves, flutes, notches, channels, or the like that may be disposed in a pattern, or in a random manner, may be used. In the embodiment shown, inner surface 37 is has a generally smooth texture. As such, this particular embodiment is adapted and/or configured to provide the outer surface 25 of the final polymer jacket 24 with a generally smooth texture. However, in other embodiments, the inner surface 37 may define a relatively rough texture, or may include a series of bumps, grooves, flutes, notches, channels, or the like that are adapted to provide the outer surface 25 with a desired surface texture and/or shape, and may be disposed in a pattern, or in a random manner. Furthermore, the cross-sectional shapes of the lumen 35 (or inner surface 37) and the outer surface 39 may be generally constant or may vary along their lengths. Additionally, the cross-sectional shape of the lumen 35 (or inner surface 37) and the outer surface 39 may be generally consistent with, or may vary with one another.

In some embodiments, the elongated tubular member 26 can be a generally tubular member having an outer diameter in the range of about 0.01 to about 0.1 inches, a lumen 35 having a diameter in the range of about 0.01 to about 0.07 inches. It should be understood, however, that these sizes and shapes are given by way of example only, and that a broad variety of other sizes and shapes may be used.

The elongated tubular member 26 can include and/or be made of any of a broad variety of materials that would allow for the appropriate functioning of the member 26, as generally discussed above. For example, the material of the member 26 can allow for appropriate heat transfer and can be sufficiently deformable and/or flexible such that when the heat and compressive force are applied, the elongated tubular member 26 can aid in retaining and/or attaching the polymer jacket member 24a to the core wire 22, and can aid in shaping and/or forming the polymer jacket member 24a. Some examples of suitable material may include any of a broad variety of polymers and metals that can have suitable characteristics.

In at least some embodiments, the material of the elongated tubular member 26 can have relatively stable physical characteristics relative to the polymer jacket member 24a at the temperatures used and/or applied during the method. For example, the elongated tubular member 26 can include material that, when heated with a predetermined amount of heat used during the method, does not melt and/or become as fluid, sticky, and/or visco-elastic as the material of the polymer jacket member 24. For example, the material of the elongated tubular member 26 can have physical characteristics, such as a melting point, softening point, $T_g$, or the like, that are at temperatures that are relatively higher than that of the material of the polymer jacket member 24a. For example, when heated to temperatures that are needed to heat the polymer jacket member 24a to the softening point temperature, the material of the elongated tubular member 26 may be less visco-elastic, less plastic and/or more viscous than the material of the polymer jacket member 24a. As such, the elongated tubular member 26 can thereby function as an outer barrier and/or forming member and/or retaining member and/or tooling member for the polymer jacket member 26 while not melting with or into the polymer jacket member 26.

For example, the material used in the elongated tubular member 26a can have a softening point similar to or above that of the softening point temperature of the polymer jacket member 24a. Similarly, in at least some embodiments, the material can generally have a melting or liquid temperature point similar to or above that of the melting or liquid temperature of the polymer jacket member 24a. Similarly, in at least some embodiments, the material can generally have a $T_g$ that is similar to or above that of the $T_g$ of the polymer jacket member 24a. For example, some embodiments utilize a tubular member 26a made from PTFE, which has a $T_g$ around room temperature, melting temperature of 335° C. PTFE may carbonize if exposed to too much heat and can act like it is thermal set even if it does not, technically, thermal set.

Likewise, the material of the elongated tubular member 26 can be suitably deformable and/or flexible at the temperatures used in the method such that the predetermined compressive force can be at least partially applied to the polymer jacket member 24a through the elongated tubular member 26. For example, in some embodiments, the material of the elongated tubular member 26 can be sufficiently deformable, for example plastically deformable, so as to deform from a first shape and/or configuration to a second shape and/or configuration when the compressive force, or other force, is applied. In some embodiments, the deformation of the tubular member 26 may be generally permanent such that the tubular member 26 generally maintains the second shape and/or configuration. In other embodiments, however, the elongated tubular member 26 can be sufficiently flexible and/or elastic such that it a can recover, at least partially, from the deformation.

In some example embodiments, the elongated tubular member 26 may be made from a fluorocarbon material, such as PTFE, FEP, PFA, CTFE, ETFE, or the like (including heat shrink varieties thereof), or may otherwise include a fluorocarbon. For example, an elongated PTFE tube may be used as the elongated tubular member 26.

Now that some examples of the general components have been describe, an example embodiment of the method can be described. In this embodiment, the method can be performed by arranging the core wire 22, the polymer jacket member 24a, and the tubular member 26 in an appropriate configuration to create the subassembly 28, for example as shown in FIG. 4. A portion of the polymer jacket member 24a can be positioned over core wire 22, and a portion of the elongated tubular member 26 can be disposed over the portion of the polymer jacket member 24a to create the subassembly 28. In some embodiments, the entire length of the polymer jacket 24 can be disposed about a portion of the core wire 22. However, in other embodiments, the polymer jacket 24 can be disposed such that it includes a first portion 60 that is disposed about a portion of the core wire 22 and a second portion 62 that extends beyond, for example distally beyond, and is not disposed about the core wire 22. For example, in some embodiments it may be desired that the polymer jacket 24 is used to form or aids in forming a tip, for example a distal tip, for the guidewire 10. Additionally, in some embodiments, the entire length of the elongated tubular member 26 can be disposed about a portion of polymer jacket member 24a and/or core wire 22. However, in other embodiments, the elongated tubular member 26 can be disposed such that it includes a first portion 70 that is disposed about a portion of polymer jacket member 24a and/or the core wire 22, and a second portion 72 that extends beyond, and is not disposed polymer jacket member 24a and/or the core wire 22.

In at least some embodiments, a concentric arrangement is achieved, wherein each of the components of the subassembly 28 extends generally along a common longitudinal axis. However, this need not be the case, as other arrangements are contemplated, for example, arrangements wherein the core wire 22 may not be centered within the polymer jacket member 24, for example, if the lumen 33 is not centered within the polymer jacket member 24a.

In some embodiments, an adhesive material may be disposed between portions of the core wire 22 and the polymer jacket member 24a. The use of such adhesive material may aid in ensuring a solid attachment between the core wire 22 and the polymer jacket 24, especially in cases where the particular polymer material used in the polymer jacket 24 may not necessarily adhere as well as desired to the particular material used for the core wire 22. As such, it should be understood, that the adhesive material is not necessary in all embodiments. Furthermore, in some cases, for example where it is desired that portions of the elongated tubular member 26 remain attached to the polymer jacket 24, an adhesive material can be disposed between portions of the polymer jacket member 24a and/or portions of the core wire 22 and portions of the elongated tubular member 26. Again, it should be understood that the adhesive material is not necessary in all embodiments. Some examples of suitable adhesive material may include THIXON®, SANCURE® (polyurethane dispersion), PLEXAR®, ADMER®, and the like, all of which are commercially available.

A predetermined amount of heat and compressive force is then applied to the subassembly 28, for example to the outer surface 39 of the elongated tubular member 26. The predetermined amount of heat and compressive force is sufficient to heat the polymer jacket member 24a so that it softens, becomes visco-elastic, and/or melts, and deforms such that it attaches to the core wire 22. In the embodiment show, the predetermined amount of heat and compressive force is applied by advancing the subassembly 28 through a heated die 30, or the like. It should be noted that although the 1o embodiment shown illustrates the subassembly 28 going through die 30 in a "distal to proximal" direction (i.e., the distal end first through die 30), passing subassembly 28 through die 30 in the opposite direction (i.e., "proximal to distal") is, of course, contemplated.

As shown, the die 30 has a first or input end 38 and a second or output end 40. The subassembly 28 can be moved such that it enters a first opening 42 adjacent first end 38 and exits through a second opening 44 adjacent the second end 40. First opening 42 is generally larger than second opening 44 so that as subassembly 28 passes through die 30 the decrease in size from first opening 42 to second opening 44 applies a compressive force, and compresses the subassembly 28. Additionally, the die 30 can be heated such that it applies heat to the subassembly 28. In some embodiments, heat is generated adjacent to the die 30 through the use of carriage heaters mounted in the die holding block (not shown) or in any other suitable manner or with any other suitable heating means. In some embodiments, subassembly 28 is fed linearly though die 30, for example, manually, or with a moving and/or pulling device, such as a linear travel crosshead device, or the like. In some embodiments, a variable speed linear travel crosshead device (not shown) can be attached to the distal portion or leading edge of the subassembly 28, and can be used to pull the subassembly 28 through the die 30, for example, through the openings 42/44. For example, the linear travel crosshead device, or other such device, may be attached to the distal portion 72 (or the proximal portion, when suitable) of the elongated tubular member 26, and is adapted to pull the subassembly through the die 30. The use of a variable speed linear travel crosshead device allows the user to change the speed that subassembly 28 feeds through die 30 and, thus, the amount of heat exposed to the subassembly. In at least some embodiments, speeds in the range of about 0.1 to about 1.2 inches per second can be utilized (e.g., about 0.5 inches per second). In addition to changes in heat exposure, variations in speed can alter the diameter of subassembly 28 (and/or guidewire 10 and/or jacket member 24). For example, as the speed of the linear travel crosshead device increases the diameter may decrease.

As the subassembly 28 advances through die 30, the heat and compressive force are at least partially transferred to the polymer jacket member 24 through the elongated tubular member 26. As the heat is transferred into the jacket member 24, the jacket member 24 is heated such that it softens, becomes visco-elastic, and/or melts (minimally, completely, or anywhere there between). For example, the heat applied can be sufficient to heat the jacket member 24 to its softening point temperature or above. In some embodiments, the heat applied can be sufficient to heat the jacket member 24 to its softening point temperature, but below that of its melting or liquid temperature. In at least some embodiments, for example where the heat is applied to the elongated tubular member 26 and transferred inwardly to the polymer jacket member 24a, the amount of heat that is ultimately applied to the core wire 22, or possibly other structures, can be significantly less than the amount of heat applied to the elongated tubular member 26 and/or the polymer jacket member 24a. As such, the core wire or other structures may experience a nominal to a significantly reduced temperature increase during the application of the heat.

Additionally, the compressive force generated by the movement of subassembly 28 through die 30 can be sufficient to cause the softened jacket member 24 to flow onto or otherwise be compressed onto core wire 22 so that it substantially conforms to the contour of core wire 22 and attaches thereto. Additionally, in embodiments including an adhesive material disposed between portions of the core wire 22 and the polymer jacket member 24a, the adhesive material can aid in attaching the polymer jacket member 24a to the core wire 22. Likewise, in embodiments including an adhesive material disposed between portions of the elongated tubular member 26 and the polymer jacket member 24a and/or the core member 22, the adhesive material can aid in attaching the elongated tubular member 26 to the polymer jacket member 24a and/or to the core wire 22. In some embodiments, the predetermined amount of heat and compressive force may also be sufficient to activate and/or soften the adhesive material. As discussed above, however, the adhesive material is not necessary in some embodiments, and in some cases, may not be desired.

The compression is best seen by referring to FIG. 5, which illustrates a side view of the subassembly 28 without the die 30 and shows a compressed or deformed portion 32 of the subassembly 28, an enlarged section 34 of the subassembly 28 that may be defined near the interface of the subassembly 28 with the die 30, and an "uncompressed" or excess portion 36 of subassembly 28. It can be readily appreciated that compressed portion 32 of subassembly 28 has a smaller outside diameter than excess portion 36.

In some embodiments, an additional force, such as a linear and/or longitudinal pulling force, may also aid in reshaping and/or applying the compression force to the jacket member 24. For example, where a pulling force is applied along the longitudinal axis of the subassembly 28, for example to pull the subassembly 28 through the die 30, the elongated tubular member 26 and/or the jacket member 24 may be stretched and/or elongated due to this longitudinal force. The stretching and/or elongation of the tubular member 26 and/or the jacket member 24, or both, can result in a general reduction of their cross-sectional area and/or diameter. This reduction in the cross-sectional area and/or diameter can result in the application of at least some compression force on portions of the subassembly 28. For example, as the stretching and/or elongation of the tubular member 26 may reduce the cross-sectional area and/or diameter of the tubular member 26, the tubular member 26 is applying a compressive force to the polymer jacket member 24. Additionally, as the stretching and/or elongation of the jacket member 24 may reduce the cross-sectional area and/or diameter of the jacket member 24a, the jacket member 24a is being compressed toward the core wire 22.

Figure 6:
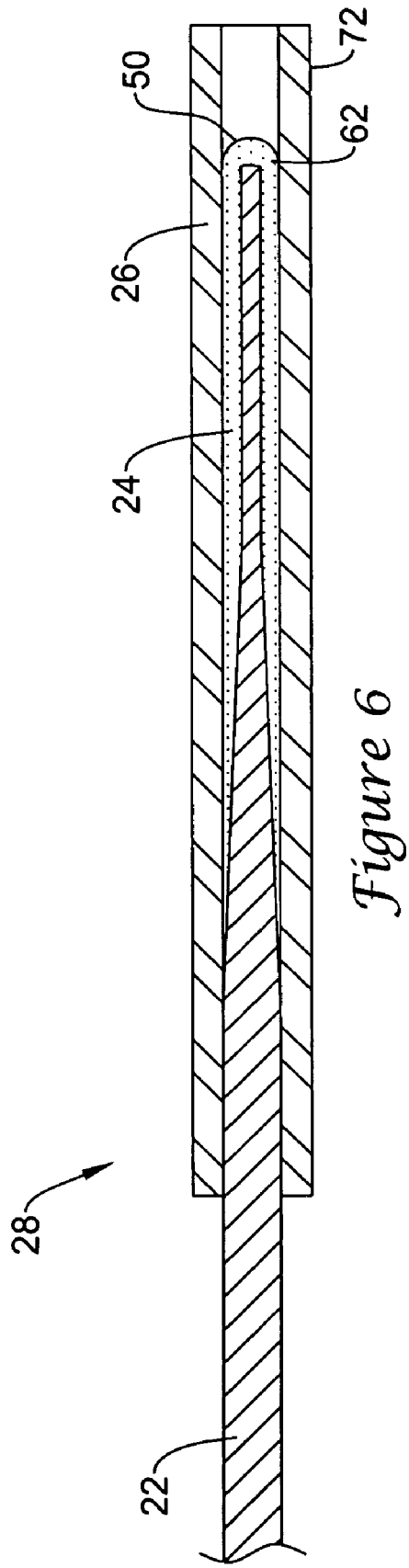
FIG. 6 is a cross-sectional side view of an example guidewire, shown after the method depicted in FIG. 4, but prior to the removal of the elongated tubular member.

After passing through the die 30, the subassembly 28 may resemble what is shown in FIG. 6. Here it can be seen that jacket member 24a has been deformed, resized and/or reshaped such that it is attached to the core wire 22, and forms a polymer jacket 24 on the core wire 22. For example, the outer diameter of the jacket member 24a has been reduced, and the inner surface 33 conforms to the shape of and is attached to core wire 22. The elongated tubular member 26 is situated on the exterior of jacket member 24, and the inner surface 37 defines the shape and/or texture of the outer surface 25 of the polymer jacket 24. The outer diameter of the elongated tubular member 26 has been reduced, and the inner surface 37 conforms to the shape of the outer surface 25 of the polymer jacket 24. The subassembly 28 may be allowed to cool, for example, such that the polymer jacket 24 may solidify or otherwise become less soft, and/or less visco-elastic than it was when heated. For example, the subassembly 28 may be allowed to cool such that the jacket member 24 cools to a point below its softening point temperature.

As can be appreciated, in at least some embodiments, that the polymer jacket member 24a can have generally solid or semi-solid physical characteristics when initially placed in the subassembly 28 configuration, and thereafter, during the application of the heat and compressive force, the physical characteristics of the polymer jacket member 24a can become at least somewhat less solid than its initial physical characteristics, and can be deformed and attached to the core wire 22 as the polymer jacket 24. Furthermore, after cooling, the polymer jacket 24 attached to the core wire 22 can regain the more solid physical characteristics, for example, similar to the initial physical characteristics of the polymer jacket member 24a. As such, at least some embodiments can be distinguished from at least some methods involving extrusion and/or co-extrusion configurations in which a polymer material is first disposed about a core wire in a liquid and/or generally flowable state.

The embodiment discussed above described the use of a single polymer jacket member 24a being used to form the polymer jacket 24 about a portion of the core wire 22. As will be appreciated by those of skill in the art and others, however, more than one polymer jacket member 24a may be used to form one or more polymer jackets 24 about the core wire 22. For example, a plurality, such as 2, 3, 4 or more polymer jacket members 24a may be used to create the subassembly 28, wherein the elongated tubular member 26 would be disposed about the outermost polymer jacket member 24a. The heat and compressive force could then be applied, for example, in accordance with the method discussed above, resulting in the softening and deforming of the multiple polymer jacket members 24a about the core wire 22 and/or about each other. In some embodiments, each of the plurality of polymer jacket members 24a may be made of or include the same materials, and through the application of the heat and compression, can form a single, thicker polymer jacket disposed about the core wire 22. In other embodiments, however, one or more of the plurality of polymer jacket members 24a may be made of or include different polymer materials from the other plurality jacket members, for example having different characteristics, thereby providing a plurality of polymer jackets disposed about the core wire 22 some of which may have differing characteristics. The use of a plurality of polymer jackets may be useful in providing the guidewire with desirable characteristics, such as flexibility, stiffness, lubricity, torquability, or the like. For example, each separate polymer layer may provide for a certain desired characteristic.

In FIG. 6, the polymer jacket 24 is shown as forming a distal tip 50 disposed adjacent the distal end of the core wire 22. In some embodiments, the heat and/or compressive force applied to attach the polymer jacket 24 to the core wire 22 may be sufficient to cause the polymer jacket 24 to deform about the distal end of the core wire 22 to form such a tip construction, for example, having a generally rounded and/or atraumatic configuration. For example, the distal portion 62 of the polymer jacket 24 as shown in FIG. 4 may be heated and compressed such that it forms the distal tip 50 as shown in FIG. 6. However, in at least some embodiments, the heat and/or compressive force may not be sufficient to form such a distal tip configuration. As such, in some embodiments, after the polymer jacket 24 is attached to the core wire 22, the distal most portion 62 of the polymer jacket 24 may be further processed to create such a distal tip 50. For example, the distal most portion 24 of the polymer jacket may be heated, reflowed, shaped, and/or ground such that it can form the distal tip 50 about the distal end of the core wire 22. In some embodiments, additional materials and/or structures, for example, additional polymer material, spring-type tips, solder ball tips, polymer ball tips, and the like, or other suitable tips may be added to form the distal tip 50. Additionally, many other tip configurations and/or methods of making a distal tip are generally known in the art, and may be used. The addition of these structures can occur in concert with the above procedures such that they are added as part of the overall manufacturing process. Alternatively, the structures can be added subsequently.

As can be appreciated, in the embodiment shown in FIGS. 4, 5, and 6, the elongated tubular member 26 has been deformed such that it maintains the general shape provided as it passed through the die 30. For example, the elongated tubular member 26 may be permanently deformed to maintain the configuration where its outer diameter has been reduced, and its inner surface 37 conforms to the shape of the outer surface 25 of the polymer jacket 24. For example, the material used in the elongated tubular member 26 may be plastically deformable at the temperatures and forces used in the method such that the forces permanently deformed the elongated tubular member 26. As such, in at least some embodiments, the elongated tubular member 26 can be attached to the outer surface 25 of the polymer jacket 24 through the use of the method. It should be understood, however, that other embodiments are contemplated wherein the elongated tubular member 26 would not permanently deform, but would rather be sufficiently flexible and/or elastic such that it could recover, at least partially, to its original size and/or shape.

In some embodiments, the elongated tubular member 26 can be removed so that a guidewire 10 including a core wire 22 and a plastic jacket 24 attached about a portion of the core wire 22 is formed, for example, as shown in FIG. 2. For example, the elongated tubular member 26 can be removed by pulling, stripping, cutting, grinding, or otherwise removing the elongated tubular member 26 from about the outer surface 25 of the polymer jacket 24. In other embodiments, the elongated tubular member 26 can remain disposed on or attached to the plastic jacket 24 as an additional layer on the guidewire, as will be discussed in more detail below.

It should be understood that the particular equipment and devices used to perform the method are given by way of example only, and that other devices and/or methods may be used to apply the predetermined amount of heat and compressive force. For example, a separate source of heat may be used to apply heat to the subassembly 28 prior to passing it through the die 30 or other such shaping device. In other embodiments, the method can be performed in a heated environment, for example, in a heated oven, or the like. Furthermore, rather than a die, an appropriate mold, cast, form, of the like may be used to apply the compressive force to the subassembly 28. Additionally, rather than a linear travel crosshead, other devices for moving the subassembly 28 may be used.

Figure 7:
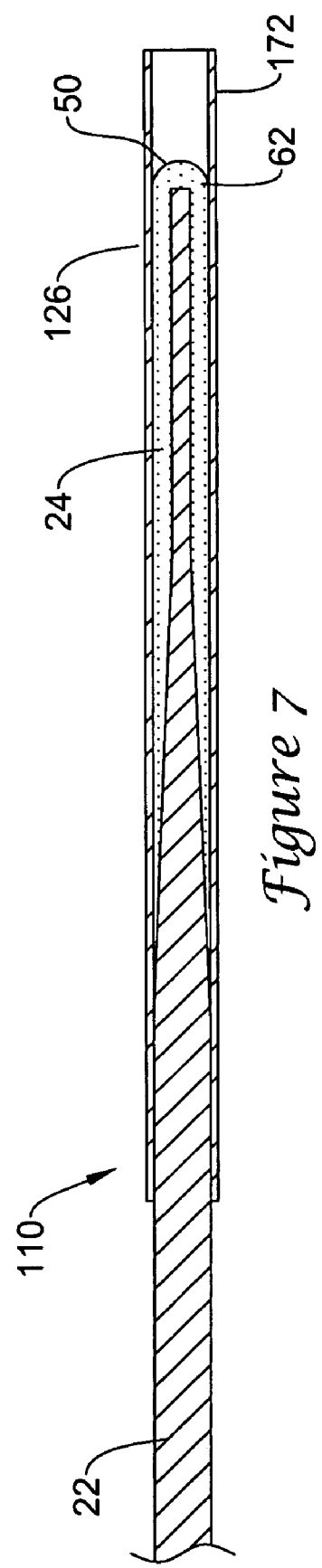
FIG. 7 is a cross-sectional view of another example embodiment of a guidewire including an elongated tubular member disposed over and attached to the polymer jacket member.

As indicated above, in some embodiments, after the polymer jacket 24 is formed and attached to the outer surface of the core wire 22, the elongated tubular member 26 can remain or be left on the guidewire, for example as an additional outer layer and/or coating. For example, refer now to FIGS. 7 and 8, which show an example of such an embodiment. In FIG. 7, the guidewire 110 is similar to the guidewire construction shown in FIG. 6, including a core wire 22 and a polymer jacket 24 formed about and attached to the core wire 22, for example using an attachment method as described above. The elongated tubular member 126 shown in this embodiment can be generally similar to and can function in a similar manner to the elongated tubular member 26 discussed above during the application of the polymer jacket 24 to the core wire 22. In this embodiment, however, elongated tubular member 26 can be adapted and/or configured to remain on and/or attached to the outer surface of the polymer jacket 24 and/or portions of the core wire 22. For example, the elongated tubular member 126 can be sufficiently "thick" so as to perform its intended purpose in attaching the polymer jacket 24 to the core wire 22, while still being "thin" enough to remain on guidewire 110, for example as a protective, lubricious, or structural layer or coating. In some embodiments, the application of the heat and compressive force used during the attachment of the polymer jacket 24 to the core wire 22 are also sufficient to plastically deform and attach the elongated tubular member 126 to the polymer jacket 24 and/or to the core wire 22. As discussed above, an adhesive material may also be used to aid in the attachment.

Figure 8:
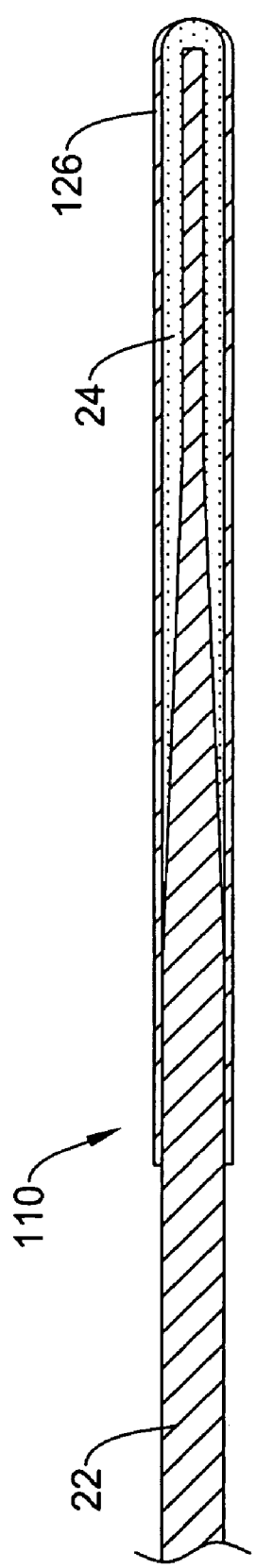
FIG. 8 is a cross-sectional side view of the guidewire depicted in FIG. 7, wherein the elongated tubular member has been altered and/or trimmed.

As can be appreciated, the elongated tubular member 126 shown in FIG. 7 includes a distal portion 172 that extends distally from the distal portion 62 of the polymer jacket 24. In at least some instances, it may be desirable to remove and/or modify the distal portion 172 so as to conform to, create and/or expose the atraumatic distal tip 50 of guidewire 110. For example, as seen in FIG. 8, the distal portion 172 may be trimmed and/or shaped such that the distal tip 50 is exposed. In other embodiments, the distal portion 172 may be shaped and/or formed, for example, through heating, reflowing, and/or grinding, or the like, so that the distal portion 172 creates and/or is a part of the distal tip 50. As indicated above, many other tip configurations and/or methods of making a distal tip are generally know in the art, and may be used.

It should also be understood that guidewires embodiments in accordance with the invention may include and/or incorporate a broad variety of other components and/or structures into the guidewire construction. For example, the guidewire may also include one or more coils, such as inner coils, outer coils, spring coils or marker coils; ribbons or wires, such as shaping or safety ribbons or wires; bands or rings, such as markers or centering bands or rings; additional coatings or polymer layers; and/or any of a broad variety of other structures generally known. Such structures may be disposed over, underneath, or encapsulated within the polymer jacket 24, or may be disposed over, about or on the core wire 22 at a location adjacent to or separate from the polymer jacket 24.

In at least some embodiments, portions or all of core wire 22, or other structures included within the guidewire 10 may also be doped with, made of, or otherwise include a radiopaque material. Radiopaque materials are understood to be materials capable of producing a sufficiently bright image on a fluoroscopy screen or another imaging technique during a medical procedure. This image aids the user of guidewire 10 in determining its location. Some examples of radiopaque materials can include, but are not limited to gold, platinum, palladium, tantalum, tungsten, polymer material loaded with a radiopaque filler, and the like. Additionally, as indicated above, the core wire 22 and/or guidewire 10 may include one or more marker bands or coils that include a radiopaque material.

In some embodiments, a degree of MRI compatibility can be imparted into guidewire 10. For example, to enhance compatibility with Magnetic Resonance Imaging (MRI) machines, it may be desirable to make core wire 22, or other portions of guidewire 10, in a manner that would impart a degree of MRI compatibility. For example, core wire 22, or portions thereof, may be made of a material that does not substantially distort the image and create substantial artifacts (artifacts are gaps in the image). Certain ferromagnetic materials, for example, may not be suitable because they may create artifacts in an MRI image. Core wire 22, or portions thereof, may also be made from a material that the MRI machine can image. Some materials that exhibit these characteristics include, for example, tungsten, Elgiloy, MP35N, nitinol, and the like, and others.

Figure 9:
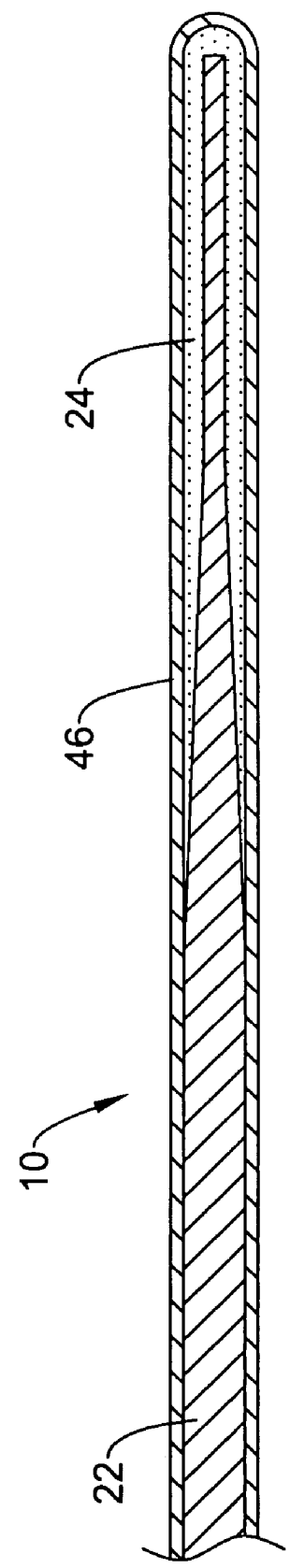
FIG. 9 is a cross-sectional view of another example embodiment of a guidewire including a coating disposed over the polymer jacket member.

Refer now to FIG. 9, which shows another embodiment of a guidewire 10 similar to that shown in FIG. 2, wherein like reference numbers are used to indicate similar structure. This embodiment of a guidewire 10 includes a core wire 22 and a polymer jacket 24, as discussed above, but also includes a coating and/or covering 46 disposed over at least a portion of the polymer jacket 24 and/or core wire 22. For example, the coating 46 may comprise a lubricious, a hydrophilic, a protective, or other type of coating that may provide guidewire 10 with desirable features. For example, hydrophobic coatings such as fluoropolymers provide a dry lubricity which improves guidewire handling and device exchanges. Lubricious coatings improve steerability and improve lesion crossing capability. Suitable lubricious polymers are well known in the art and may include silicone and the like, hydrophilic polymers such as polyarylene oxides, polyvinylpyrolidones, polyvinylalcohols, hydroxy alkyl cellulosics, algins, saccharides, caprolactones, and the like, and mixtures and combinations thereof. Hydrophilic polymers may be blended among themselves or with formulated amounts of water insoluble compounds (including some polymers) to yield coatings with suitable lubricity, bonding, and solubility. Some other examples of such coatings and materials and methods used to create such coatings can be found in U.S. Pat. Nos. 6,139,510 and 5,772,609, which are incorporated herein by reference. In the embodiment shown, the coating is disposed about the polymer jacket 24 and about a portion of or all of the remaining core wire 22. In other embodiments, however, the coating may be disposed only about the polymer jacket 24, or only about the portion of the core wire 22 not including the polymer jacket Coating 46 may be formed, for example, by coating, extrusion, co-extrusion, interrupted layer co-extrusion (ILC), or fusing several segments end-to-end over guidewire 10. The layer may have a uniform stiffness or a gradual reduction in stiffness from the proximal end to the distal end thereof. The gradual reduction in stiffness may be continuous as by ILC or may be stepped as by fusing together separate extruded tubular segments. The outer layer may be impregnated with a radiopaque filler material to facilitate radiographic visualization. Those skilled in the art will recognize that these materials can vary widely without deviating from the scope of the present invention.

Figure 11:
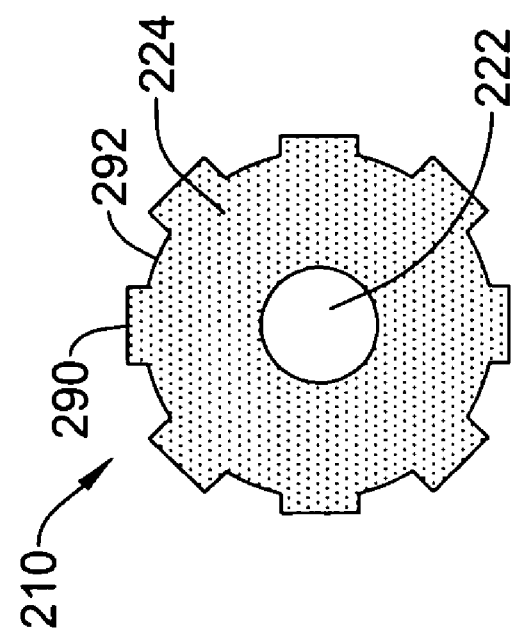
FIG. 11 is a cross-sectional view of the example guidewire depicted in FIG. 10, shown with the elongated tubular member removed, and the outer surface of the polymer jacket member having a desired cross-sectional shape.
Figure 10:
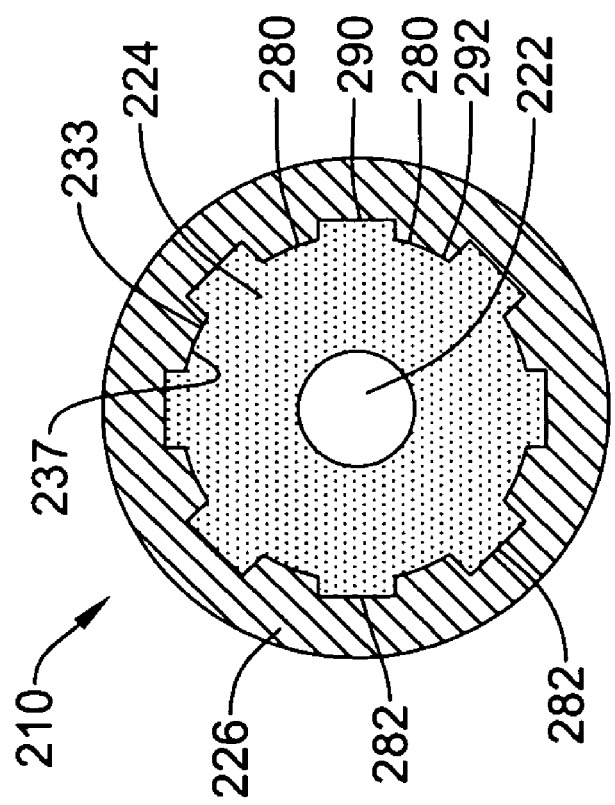
FIG. 10 is a cross-sectional view of another example embodiment of a guidewire construction, showing the elongated tubular member having an inner surface that shapes the outer surface of the polymer jacket member.

As discussed above, the elongated tubular member, for example 26 or 126, may include an inner surface 37 that can be adapted and/or configured such that, when the heat and compressive force is applied, aids in shaping and/or forming the outer surface 25 of the polymer jacket member 24a to include a desired shape and/or texture. Refer now to FIGS. 10-11, which illustrate another of the many alternatives to the shape and/or configuration of an elongated tubular member that may be used.

FIG. 10 is a cross-sectional view of a subassembly 228 shown after the heat and compressive force have been applied to compress and/or deform the elongated tubular member 226 onto the polymer jacket member 224, and to attach the polymer jacket member 224 to the core wire 222. As can be seen, the inner surface 237 of the elongated tubular member 226 includes a plurality of flutes and/or raised portions 280 separated by a plurality of notches or grooves 282. These flutes 280 and grooves 282 may extend over one or more portions of, or along the entire length of, the elongated tubular member 226, and may or may not be disposed in a generally concentric pattern, as shown. As can be appreciated, when the elongated tubular member 226 is compressed and/or deformed onto the outer surface 233 of the polymer jacket member 224 during the application of the heat and compressive force, the outer surface 233 of the softened polymer jacket member 224 can conform to the shape defined by the inner surface 237. As such, the outer surface 233 is provided at least somewhat with a shape that is generally a mirror image of the shape of the inner surface 237, and therefore includes a plurality of flutes and/or raised portions 290 separated by a plurality of notches or grooves 292. In some embodiments, the elongated tubular member 226 can be removed, for example as shown in FIG. 11, to expose the outer surface 233 of the polymer jacket member 224. As can be appreciated, this embodiment is given by way of example only, and any of a broad variety of shapes and/or textures can be provided to the outer surface 233 of the polymer jacket member 224.

As can be appreciated by those of skill in the art and others, in at least some embodiments, the methods of making a guidewire and/or attaching a polymer jacket member to a core wire as discussed herein may provide certain advantages and/or benefits. For example, in some embodiments, the polymer jacket member can be provided with a desired shape, texture, size and/or thickness, and 1n some cases without the need for excessive, or in some embodiments, any additional grinding and/or smoothing steps. Additionally, some embodiments may allow for fewer and/or reduced exposure of the core wire or other structures in the guidewire to thermal conditions that may cause alterations of temperature-related properties and characteristics associated with guidewire. For example, in some embodiments, the core wire 22, or other structures within the guidewire 10, may include materials that may be temperature sensitive. For example, the guidewire may include structures that include shape memory material and/or a superelastic (pseudoelastic) material, the properties of which may be that may be at least somewhat temperature sensitive. In some embodiments of the method described herein, the temperature and number of the thermal exposures may be decreased relative to other commonly used methods.

It should be understood that this disclosure is, in many respects, only illustrative. Changes may be made in details, particularly in matters of shape, size, and arrangement of steps without exceeding the scope of the invention. The invention's scope is, of course, defined in the language in which the appended claims are expressed.

What is claimed is:

1. A method for manufacturing a medical guidewire, the method comprising:
    providing an elongated core member defining an outer surface;
    disposing an polymer jacket member about at least a portion of the outer surface of the elongated core member, wherein the polymer jacket member comprises a thermoplastic polymer material;
    providing an elongated tubular member having an undeformed state and including an inner surface defining a lumen, and defining an outer surface;
    disposing the elongated tubular member about at least a portion of the polymer jacket member, wherein the portion of the polymer jacket member and a portion of the core member are disposed within the lumen;
    applying heat and compressive force to the outer surface of the elongated tubular member such that the portion of the polymer jacket member is heated to or above a predetermined temperature at which the thermoplastic polymer material softens and such that the softened portion of the polymer jacket member is deformed to attach to the core member;
    wherein the elongated tubular member is configured to at least partially recover to the undeformed state when the heat and compressive force is removed; and
    removing the elongated tubular member from the polymer jacket member.

2. The method of claim 1, wherein the predetermined temperature is at or above the softening point temperature of the thermoplastic polymer material.

3. The method of claim 1, wherein the predetermined temperature is at or above the $T_g$ and at or below the melting point temperature of the thermoplastic polymer material.

4. The method of claim 1, wherein the predetermined temperature is above the $T_g$ of the thermoplastic polymer material.

5. The method of claim 1, wherein the predetermined temperature is below the melting point temperature of the thermoplastic polymer material.

6. The method of claim 1, wherein when heated to or above a predetermined temperature, the thermoplastic polymer material is more visco-elastic than when at temperatures below the predetermined temperature.

7. The method of claim 1, wherein when heated to or above a predetermined temperature, the thermoplastic polymer material is less viscous than when at temperatures below the predetermined temperature.

8. The method of claim 1, wherein the elongated tubular member comprises a polymer material, and wherein when the predetermined amount of heat and compressive force is applied such that the thermoplastic polymer material is heated to or above the predetermined temperature, the material of the elongated tubular member is not as soft as the thermoplastic polymer material.

9. The method of claim 1, wherein the elongated tubular member comprises a polymer material, and wherein when the predetermined amount of heat and compressive force is applied such that the thermoplastic polymer material is heated to or above the predetermined temperature, the material of the elongated tubular member is less visco-elastic than the thermoplastic polymer material.

10. The method of claim 1, wherein the elongated tubular member comprises a polymer material, and wherein when the predetermined amount of heat and compressive force is applied such that the thermoplastic polymer material is heated to or above the predetermined temperature, the material of the elongated tubular member is more viscous than the thermoplastic polymer material.

11. The method of claim 1, wherein the predetermined amount of heat Applied is not sufficient to render the elongated tubular member softer than the polymer jacket member.

12. The method of claim 1, wherein the predetermined amount of compressive force is applied by passing the subassembly through a die.

13. The method of claim 1, wherein the predetermined amount of heat is applied by the use of a heating device.

14. The method of claim 1, wherein the predetermined amount of heat and compressive force is applied by passing the subassembly through a heated die.

15. The method of claim 1, further including disposing an adhesive material between a portion of the core member and a portion of the polymer jacket member.

16. The method of claim 1, wherein the predetermined amount of heat and compressive force applied to the outer surface of the elongated tubular member compresses the elongated tubular member onto the polymer jacket member, and compresses the polymer jacket member onto the core wire.

17. The method of claim 16, wherein the polymer jacket member defines an outer surface, and when the elongated tubular member is compressed onto the polymer jacket member, the inner surface of the elongated tubular is compressed onto the outer surface of the inner tubular member.

18. The method of claim 17, wherein the inner surface of the elongated tubular member includes a predetermined shape or texture, and when the inner surface of the elongated tubular is compressed onto the outer surface of the inner tubular member, a negative mold of the predetermined shape or texture is at least partially transferred to the outer surface of the polymer jacket member.

19. The method of claim 18, wherein the predetermined shape or texture includes a smooth texture, or one or more bumps, grooves, flutes, notches, or channels.

20. The method of claim 1, wherein the elongated tubular member has a first outside diameter prior to the application of the heat and compressive force, and wherein the elongated tubular member has a second outside diameter smaller than the first outside diameter after the application of the heat and compressive force.

21. A method for manufacturing a guidewire, the method comprising:

providing a guidewire core, a thermoplastic polymer jacket member, and an elongate tubular member comprising a fluoropolymer;

creating a subassembly by disposing the thermoplastic polymer jacket about a portion of the core, and disposing the elongate tubular member about a portion of thermoplastic polymer jacket;

advancing the subassembly through a heated die which applies heat and a compressive force to the subassembly such that the polymer jacket is softened and compressed onto and attaches to the guidewire core;

wherein the elongated tubular member is configured to at least partially recover to its original size or shape following the advancing step; and removing the elongate tubular member.

* * * * *

UNITED STATES PATENT AND TRADEMARK OFFICE
CERTIFICATE OF CORRECTION

PATENT NO. : 7,651,578 B2
APPLICATION NO. : 11/449166
DATED : January 26, 2010
INVENTOR(S) : Sharrow et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 594 days.

Signed and Sealed this

Twenty-third Day of November, 2010

David J. Kappos
*Director of the United States Patent and Trademark Office*